United States Patent
Risse

[11] Patent Number: 5,993,640
[45] Date of Patent: Nov. 30, 1999

[54] METHOD OF MEASURING THE CACO₃ CONTENT OF A SCRUBBING SUSPENSION, ESPECIALLY FOR A FLUE GAS DESULFURIZING ABSORBER

[75] Inventor: Theo Risse, Werne, Germany

[73] Assignee: Lurgi Lentjes Bischoff GmbH, Essen, Germany

[21] Appl. No.: 09/127,431

[22] Filed: Jul. 31, 1998

[30] Foreign Application Priority Data

Aug. 1, 1997 [DE] Germany ............................ 197 33 284

[51] Int. Cl.⁶ .......................... G01N 27/26; G01N 33/00
[52] U.S. Cl. ...................... 205/782; 204/433; 205/787.5; 436/79; 436/133; 436/163
[58] Field of Search .................... 204/420, 433; 205/782, 787.5; 436/79, 133, 145, 146, 163

[56] References Cited

U.S. PATENT DOCUMENTS

| | | | |
|---|---|---|---|
| 4,397,957 | 8/1983 | Allison | 436/133 |
| 4,424,276 | 1/1984 | Clark et al. | 205/782 |
| 4,677,077 | 6/1987 | Onizuka et al. | 436/133 |
| 5,001,070 | 3/1991 | Ivaska et al. | 205/787.5 |
| 5,158,894 | 10/1992 | Kurzinger | 436/133 |

FOREIGN PATENT DOCUMENTS 38 09 379  11/1988  Germany.

*Primary Examiner*—T. Tung
*Attorney, Agent, or Firm*—Herbert Dubno

[57] ABSTRACT

The $CaCO_3$ content of a scrubbing suspension, especially for a desulfurizing apparatus for flue gas is measured by injecting an acid into a constant mass flow of the suspension circulating along a bypass and measuring the pH before and after such injection. The change in pH is compared with reference measurements and used as a basis for calculating the $CaCO_3$ concentration.

8 Claims, 4 Drawing Sheets

METHOD OF MEASURING THE CACO₃ CONTENT OF A SCRUBBING SUSPENSION, ESPECIALLY FOR A FLUE GAS DESULFURIZING ABSORBER

FIELD OF THE INVENTION

My present invention relates to a method of measuring the $CaCO_3$ content of a scrubbing suspension, especially a scrubbing suspension formed in a flue gas desulfurizing absorber.

BACKGROUND OF THE INVENTION

In the processing of flue gases, especially from fossil fuel power plants and the like, the flue gas may be scrubbed in a desulfurization unit having a desulfurization scrubber or absorber in which the flue gas is brought into direct contact with a scrubbing solution containing calcium carbonate ($CaCO_3$), the scrubbing liquid collecting as a suspension in the sump of the absorber.

It is important to be able to measure the $CaCO_3$ content of the suspension withdrawn from the sump of the absorber. Based upon this measurement, limestone metering to the scrubbing solution, namely, the addition of fresh limestone, can be controlled or determined. In the past the technique for such measurement has involved the taking of samples and subjecting the samples to a laboratory analysis for the $CaCO_3$ content. This procedure has been expensive and, of necessity, the time between individual measurement or sampling has been excessive because each sampling was associated with an expensive analytical step.

The automated measuring system has been proposed to allow the $CaCO_3$ content values to be obtained with shorter intervals. For example, DE-C 38 09 379 describes a continuous process in which a measurement stream is branched from the scrubbing plant or absorber, acid is added to the measurement stream to drive out $CO_2$, partial values for $CO_2$ like partial pressure can be measured and the $CaCO_3$ content calculated for the branched measurement stream from the partial $CO_2$ value. The precision and sensitivity of this process, however, leaves much to be desired.

OBJECTS OF THE INVENTION

It is, therefore, the principal object of the present invention to provide a measuring process, especially for a flue gas desulfurization apparatus, which can be automated and provides continuously a measurement with sufficient precision for the control of the addition of $CaCO_3$ to the suspension for example and which, in general terms, affords improved precision and sensitivity over earlier systems.

Still another object of the invention is to provide a continuous system for the measurement of the $CaCO_3$ content of the absorber suspension for a desulfurization plant whereby drawbacks of earlier systems can be obviated.

SUMMARY OF THE INVENTION

These objects and others which will become apparent hereinafter are attained, in accordance with the invention, in a measurement process or method wherein a predetermined constant measurement stream is continually fed in a bypass through a pH measuring unit and the bypassed solution is continuously subjected to a measurement of the pH value. At time-spaced intervals, i.e. intermittently and preferably periodically, at an injection location upstream of the pH measurement unit and along the bypass path, an acid is injected into the bypassed suspension and the change in pH resulting from this injection is then measured at the pH measuring unit.

The difference between the two pH measurements, i.e. the measurement made without acid injection and the measurement made following acid injection, is then determined and compared with data from reference measurements as a function of the residence time of the suspension between injection and measurement along the path to yield the $CaCO_3$ content of the suspension.

The acid inoculation into the bypassed stream reduces the pH value therein. The invention is based upon my discovery that the gradient of the pH drop, resulting from that injection of acid, is a function of the $CaCO_3$ content of the suspension and allows a very accurate determination of the $CaCO_3$ content which can be used to determine the amounts of $CaCO_3$ which must or should be added to the suspension when the latter is recirculated as the absorbing liquid or desulfurizing absorbent.

As the $CaCO_3$ concentration of the scrubbing suspension is greater, the greater is the decrease in the pH values within a predetermined time interval. The dependency of the $CaCO_3$ content on the gradient with which the pH value of the suspension falls with acid addition, is significant and is used in accordance with the invention as a measurement of the $CaCO_3$ concentration. The duration or residence time in which the measurement stream is in the portion of the path between the point of injection of the acid and the pH measurement unit serves as the time interval in which the decrease in the pH value is measured. The greater the residence time, the greater will be the pH difference. The residence time which is employed can be easily selected by varying the distance between the injection point and the pH measuring unit, i.e. the length of the flue path between the injection point and the pH measuring unit. Good results are obtainable when this residence time is adjusted to lie in the range between 30 and 90 seconds.

The reference measurements can be made with a standard suspension bypassing the same in a continuous flow through a similar or the same apparatus and by injecting acid into it, the data with respect to the change in pH or the known $CaCO_3$ concentration being stored in memory or provided in tabular form.

In a preferred embodiment of the invention, however, the reference measurements are carried out with standard suspensions with defined $CaCO_3$ concentrations in a stirred vessel, injected with acid and with measurements of the fall in the pH value as a function of time, starting from the injection instant as $t=0$. From such measurements, a function $$F\ (CaCO_3, \Delta pH, t_1)$$

can be defined in which the $CaCO_3$ concentration of a standard suspension is associated with a decrease in the pH value $\Delta pH$ for a given point in time $t_1$. The point in time $t_1$ is, of course, so selected that it will correspond to the residence time in which the measurement stream passes from the acid injection location to the pH measurement unit. The reference measurements in this case can be carried out in simple laboratory apparatus.

The injected acid is preferably a mineral acid, especially dilute HCl solution.

When reference is made herein to injection of the acid I intend to mean a metering of an acid whose concentration and quantity is so selected with respect to the bypassed suspension medium flow that a meaningful measurement signal in terms of $\Delta pH$ can be obtained. The injected volume and concentration of the acid will also be constant, since the bypassed flow of the suspension is likewise constant, the measurements are highly reproducible.

If necessary to increase the residence time between the injection location and the pH measurement unit, residence time increasing measures can be taken, for example, by providing loops of tubing through which the suspension may flow or by subdividing the flow into tube bundles which can be added or removed from the path, etc. It is also possible to provide along the path between the injection location and the pH measuring unit vessels or chambers into which the suspension can be passed.

In order to improve the measurement precision and reliability, the measuring stream can pass in succession through a plurality of measurement units arranged in succession along the path of the bypass loop and detecting successive pH values downstream from the injection location and providing data which can be compared with the reference measurements. This arrangement allows the determination of $\Delta pH$ at each of a number of measurement stations with different residence times to be compared with corresponding data. A plurality of measurement stations may also be used when an average value is to be obtained.

BRIEF DESCRIPTION OF THE DRAWING

The above and other objects, features, and advantages will become more readily apparent from the following description, reference being made to the accompanying drawing in which.

SPECIFIC DESCRIPTION

Figure 5:
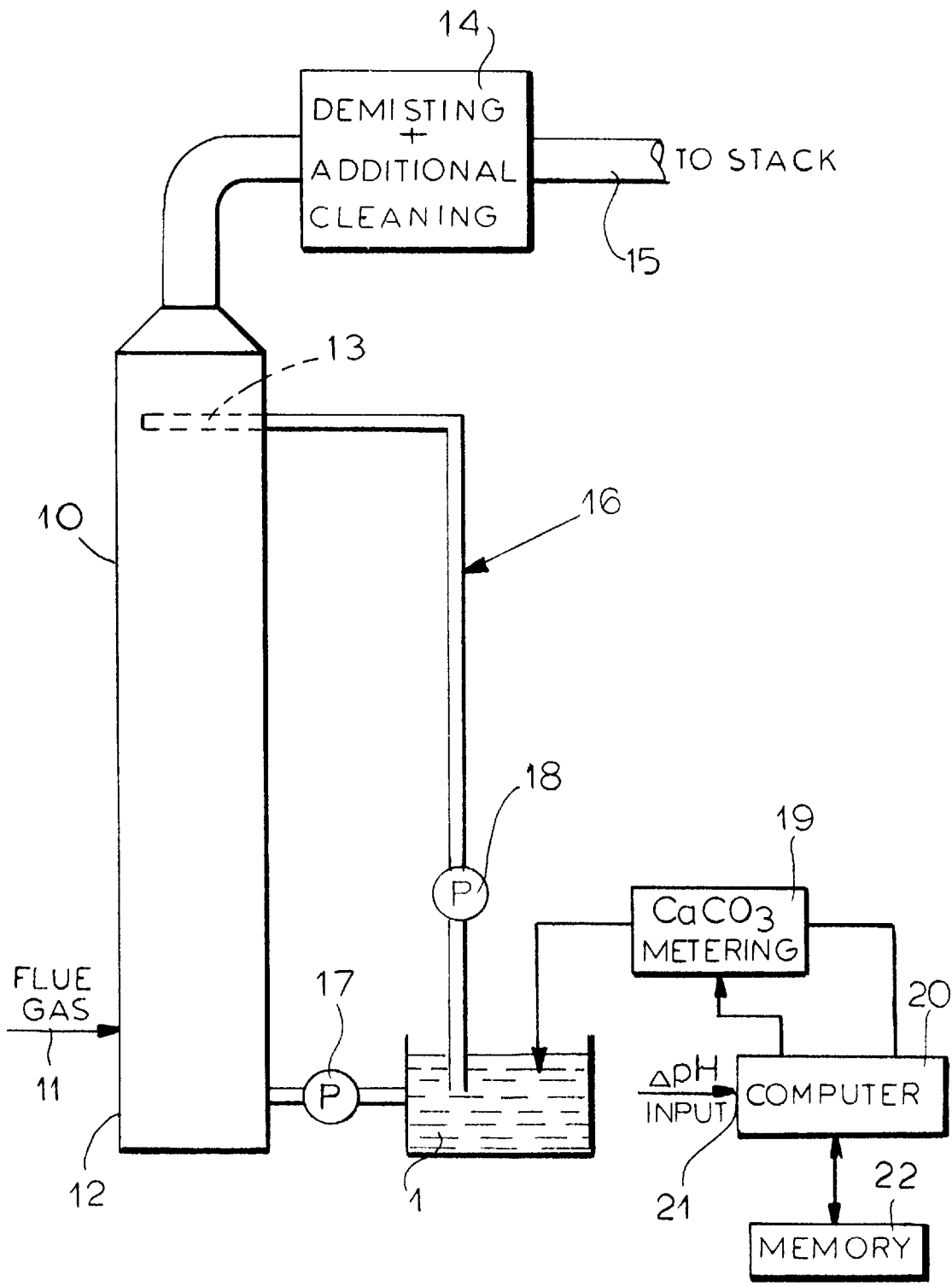
FIG. 5 is a diagram of a desulfurization plant provided with the measurement system of the invention.

Referring first to FIG. 5, it can be seen that a scrubber 10 for the desulfurization of a flue gas admitted to a lower portion of the scrubber at 11 can be effected by passing that flue gas in counterflow to a scrubbing suspension which is sprayed into the scrubbing column from a nozzle assembly 13, the scrubbing assembly having a sump 12 at which the suspension is collected. The desulfurized flue gas can be demisted and subjected to additional cleaning at 14 before being released into the atmosphere through a stack as represented at 15.

The tank 1, forming part of the absorber of the flue gas desulfurizing plant, forms part of a scrubbing liquid recirculation cycle 16 which may be equipped with a pump 17 that is withdrawing sump liquid from the absorber and a pump 18 circulating that sump liquid to the nozzle assembly.

Figure 1:
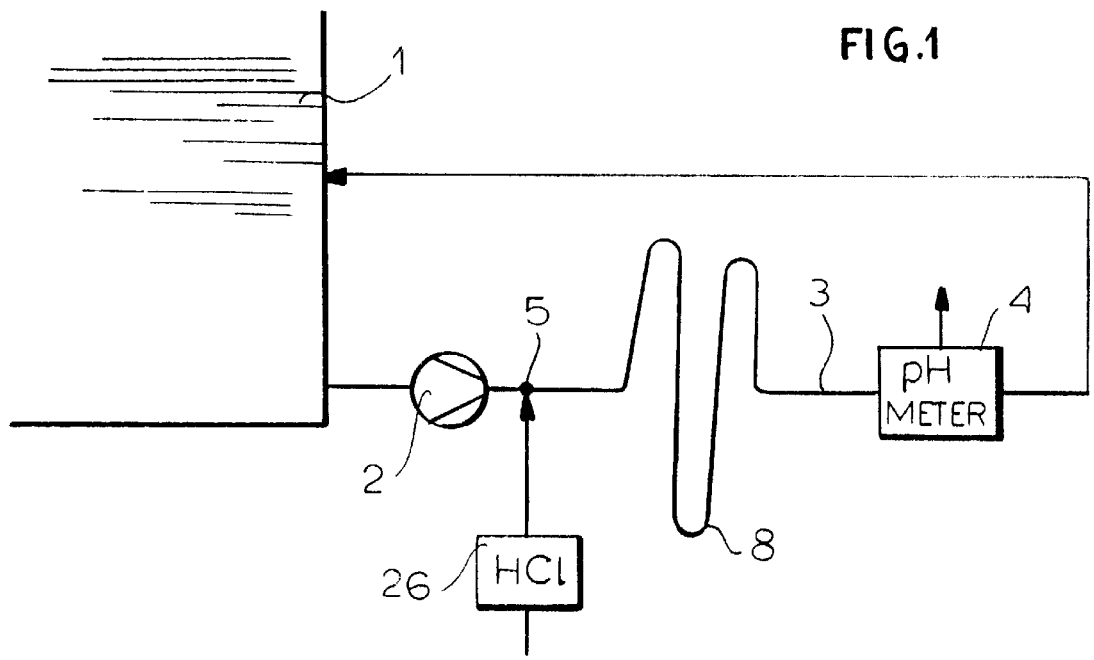
FIG. 1 is a diagram of a measurement device for measuring the $CaCO_3$ content of a scrubbing liquid suspension used in a flue gas desulfurization plant.
Figure 2:
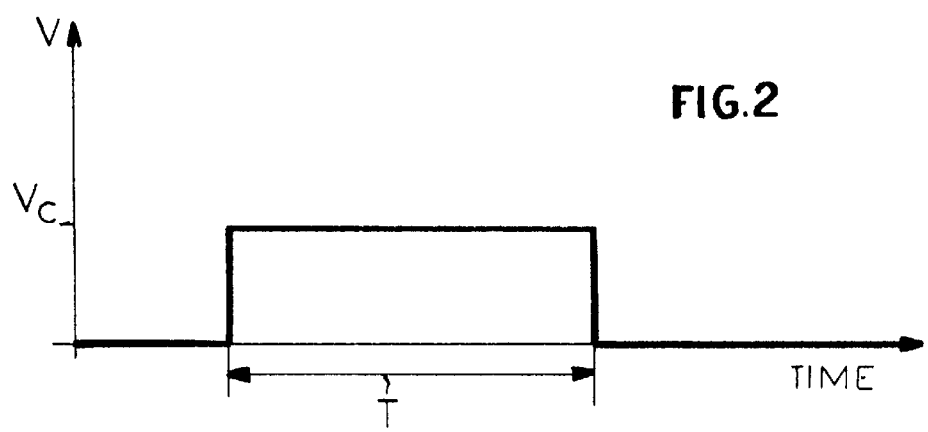
FIG. 2 is a graph indicating the injection volume of acid as a function of time into the bypass stream of the scrubbing suspension.

The tank 1 may form part of the sump of the absorber 10 and $CaCO_3$ (limestone) or a compound forming limestone such as lime, may be added via a metering device 19. The metering device 19 is controlled by a computer 20 which receives an input at 21 from the measuring unit 4 shown in FIG. 1, and can also be connected to a memory 22 symbolically representing the stored reference data with which the measured pH is compared.

Turning then to FIGS. 1–4, it will be apparent that the absorber and especially tank 1 can be provided with a bypass line 3 through which a predetermined constant mass flow of the scrubbing suspension can be circulated by means of a metering pump 2. The bypass line is represented at 3 and it will be apparent that the bypassed flow continuously traversed a pH measurement unit 4 which provides an input to the computer 20 as has been described. In the absence of inoculation with acid, the value supplied by the pH meter 4 is the pH value of the suspension, referred to herein as the starting pH value.

From time to time, at a location 5 upstream of the pH meter 4 an aqueous acid solution, especially aqueous HCl, is metered into the continuous measurement stream via a metering pump 26. The acid is injected over a duration T (FIG. 2) which is longer than the residence time for the bypassed suspension between the injection site 5 and the pH meter 4. The injected volume is constant at $V_c$.

Figure 3:
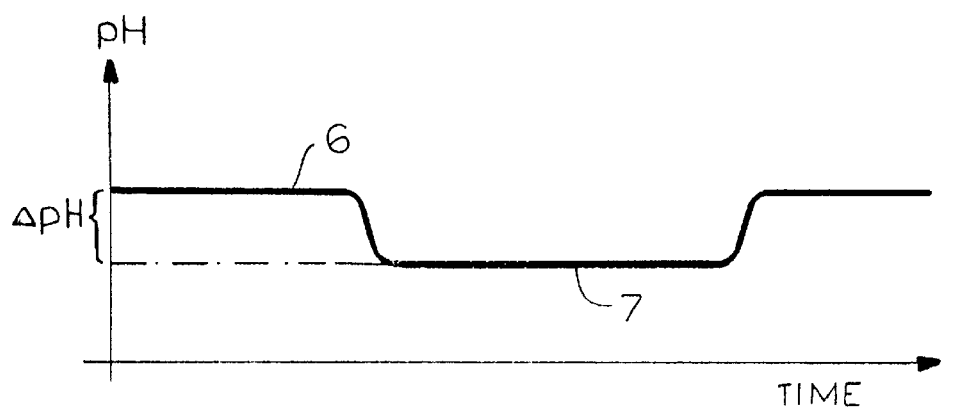
FIG. 3 is a graph showing the change in pH as a result of that acid injection.

As can be seen from FIG. 3, because of the acid injection, the pH value of the measurement stream drops. The pH difference represented as $\Delta pH$ in FIG. 3, is the difference between the starting pH value and the pH measurement resulting from the addition of acid. This measured pH value 7 is a measurement of the $CaCO_3$ content of the scrubbing suspension. By a comparison with reference measurements, the actual $CaCO_3$ concentration can be obtained (see FIG. 4).

For the reference measurements, standard suspensions with defined $CaCO_3$ concentrations are inoculated in a stirred vessel with acid, e.g. HCl solution. The drop in the pH value as a function of time from the injection instant t=0 is measured. From the measured variations, a function $$F\ (CaCO_3,\ \Delta pH,\ t_1)$$

can be established which expresses the $CaCO_3$ concentration of the standard suspension for each drop in pH value F to a fixed point in time $t_1$ after inoculation with the acid.

Figure 4:
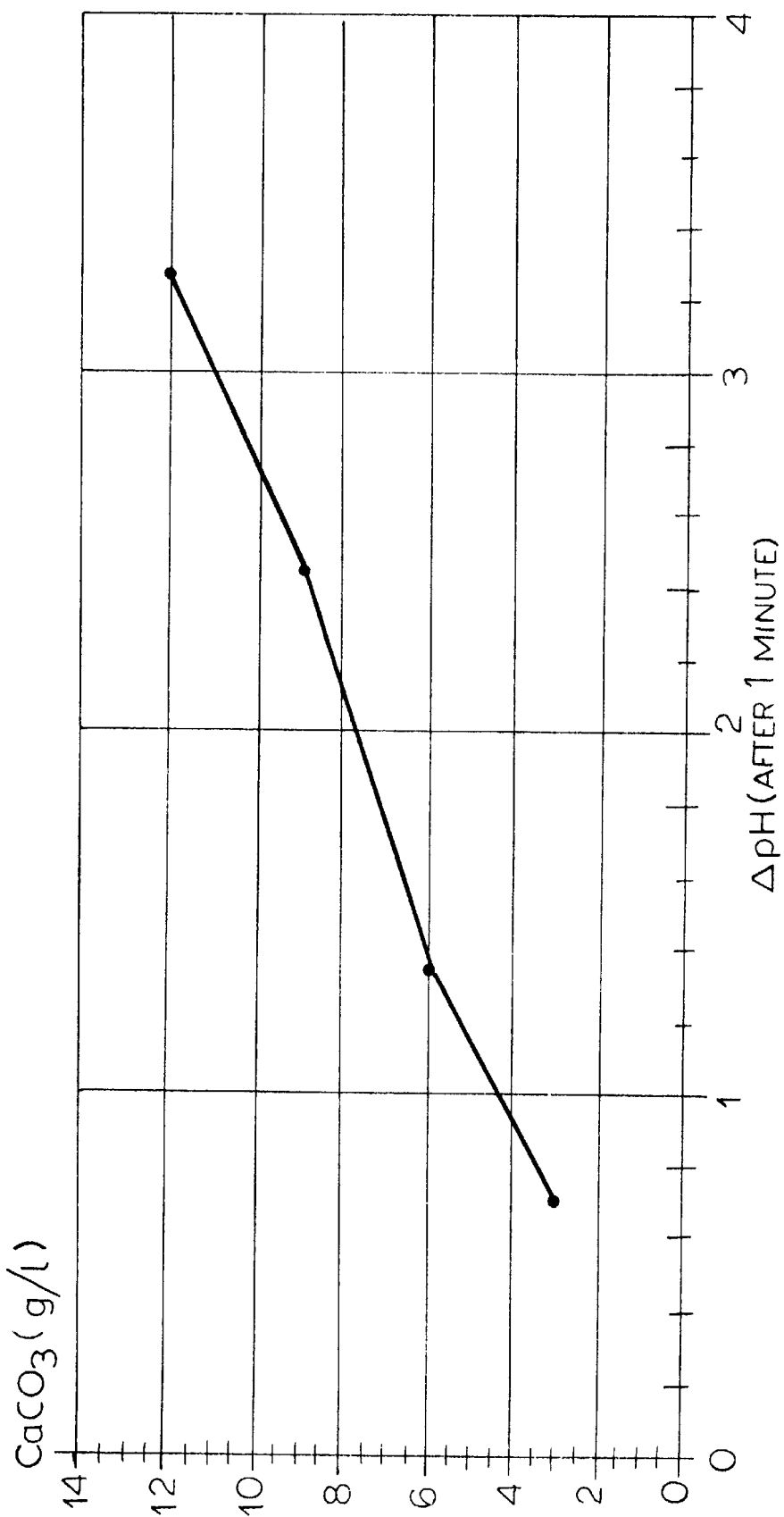
FIG. 4 is a graph showing the dependency between $CaCO_3$ concentration, plotted along the ordinate with measured decrease in pH value plotted along the abscissa after acid injection.

In FIG. 4 this dependency has been shown. From FIG. 4 it will be apparent that the dependency is an approximately linear one between the $CaCO_3$ concentration and the pH difference F. The time point $t_1$ is so selected that it corresponds to the residence time in which the inoculated measurement flow of the suspension travels the path from the injection point 5 to the pH meter 4.

In the embodiment of FIG. 3, 100 $cm^3$ of HCl solution (0.1 mol/liter concentration) is mixed with a quantity of 70 $cm^3$ of the suspension in which the $CaCO_3$ concentration varies between 3 and 12 g/l. With constant stirring, the pH drop relative to the starting pH value of 6 is measured after a duration of one minute. The change in pH $\Delta pH$ is plotted against the $CaCO_3$ concentration. Within the period of measurement, i.e. after one minute, the decrease in the pH is greater as the $CaCO_3$ concentration is larger.

Using the measurement process of the invention it should be insured that the residence time in which the suspension travels from the injection point 5 to the pH meter 4 is substantially the same as the time interval $(t=0, t_1)$ in which the function F is effective. The residence time can be adjusted by variation of the flow velocity or by the length of the flow path. To increase the flow path between the location 5 and the pH meter 4, the flow path can be looped as shown at 8. The residence time should be between 30 and 90 seconds.

Figure 6:
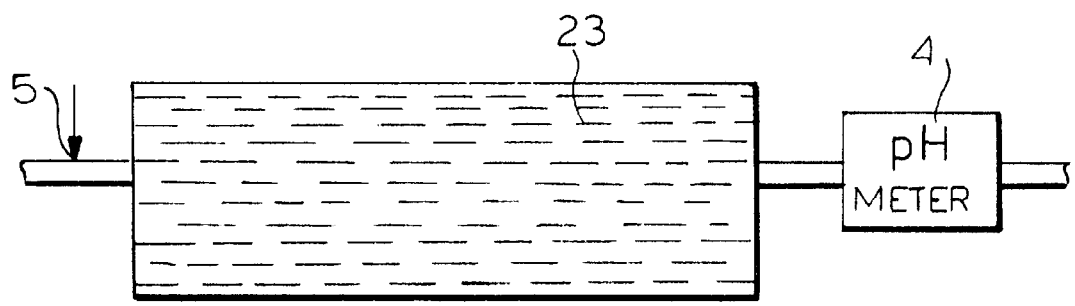
FIG. 6 is a diagram illustrating another system for increasing residence time.
Figure 7:
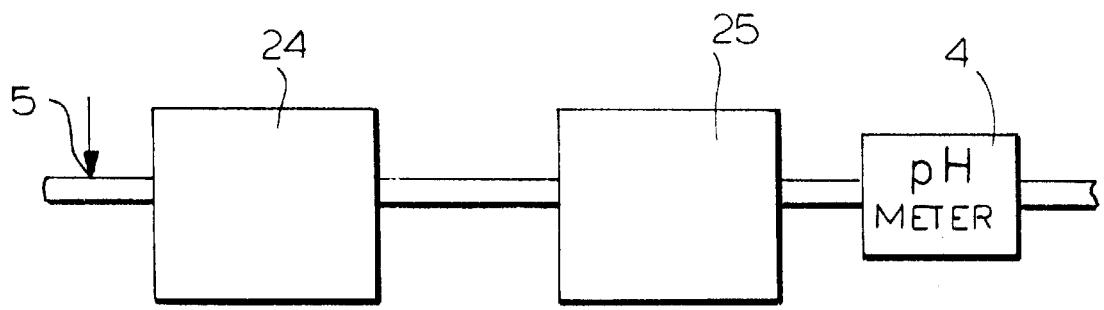
FIG. 7 is a diagram of still another system for increasing residence time.
Figure 8:
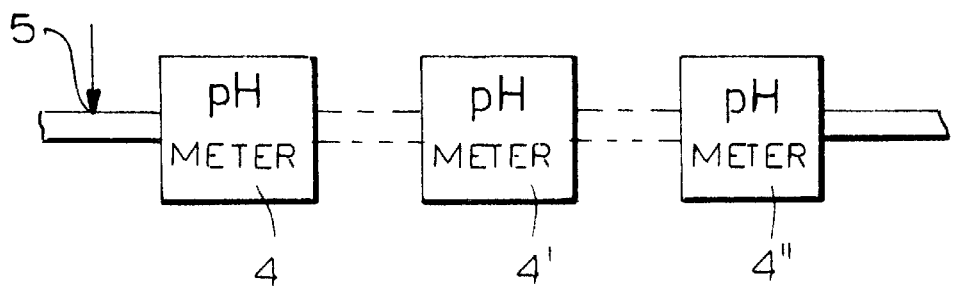
FIG. 8 is a diagram showing a cascade of pH measuring units, according to the invention.

Alternatively, a tube bundle 23 of parallel tubes can be connected between the injection point 5 and the pH meter 4 as has been shown in FIG. 6 or a number of chambers or vessels 24, 25 can be provided in cascade between the pH meter 4 and the injection point 5. It is also possible to provide spaced apart pH meters for 4', 4" as shown in FIG. 8 downstream of the injection point 5 along the path of the continuously recirculating suspension. In all cases, the measured pH values are compared with reference data and the concentration of the calcium carbonate detected so that additional calcium carbonate can be metered at 19 into scrubbing solution as desired.

I claim:

1. A method of measuring $CaCO_3$ content of a scrubbing suspension for a flue gas scrubber, comprising the steps:

continuously circulating a predetermined constant mass flow of said suspension along a bypass;

measuring pH of said suspension at a pH meter traversed by said suspension along said bypass;

intermittently injecting an acid into said suspension at a location upstream of said pH meter;

determining a change in pH $\Delta pH$ resulting from injection of acid at said location; and from measured values of $\Delta pH$ as a function of a residence time of said suspension between said location and said pH meter by comparison with reference measurements, calculating a $CaCO_3$ content of the suspension.

2. The method defined in claim 1 wherein reference measurements are made by introducing acid into standard suspension with predetermined $CaCO_3$ concentrations in a stirred vessel and measuring a resulting drop in pH values as a function of time from a time point t=0 at the introduction of the acid into the standard suspension to establish a function relating change in pH to concentration as a function of time, thereby establishing at a time point $t_1$ corresponding to said residence time, a relationship between change in pH and $CaCO_3$ concentration.

3. The method defined in claim 1 wherein said acid is a mineral acid.

4. The method defined in claim 3 wherein said acid is dilute hydrochloric acid.

5. The method defined in claim 1 wherein said acid is introduced into said suspension over a measurement time interval which is longer than said residence time.

6. The method defined in claim 1, further comprising the step of increasing said residence time by passing said suspension between said location and the pH meter through a looped tubing.

7. The method defined in claim 1, further comprising the step of increasing said residence time between said location and said pH meter by passing said suspension through a tube bundle of parallel tubes.

8. The method defined in claim 1 wherein along said bypass said suspension is passed in succession through a plurality of pH meters.

* * * * *